United States Patent [19]

Harney et al.

[11] 4,376,784

[45] Mar. 15, 1983

[54] PESTICIDAL FLUORINATED ESTERS OF THE PYRETHRIN OR PYRETHROID TYPE

[75] Inventors: Donald W. G. Harney, Doncaster; Peter G. Lehman, Tullamarine; Joseph C. Rundle, Nunawading, all of Australia

[73] Assignee: ICI Australia Limited, Melbourne, Australia

[21] Appl. No.: 246,931

[22] Filed: Mar. 24, 1981

Related U.S. Application Data

[62] Division of Ser. No. 46,757, Jun. 8, 1979, Pat. No. 4,283,414.

[30] Foreign Application Priority Data

Jun. 21, 1978 [AU] Australia .............................. PD 4813

[51] Int. Cl.³ ..................... C07C 69/614; A01N 37/10

[52] U.S. Cl. ............................... 424/304; 260/465 D; 424/308; 424/309; 560/9; 560/20; 560/22; 560/23; 560/55; 560/104; 560/107

[58] Field of Search ................... 560/105, 104, 20, 22, 560/23, 89, 55, 107; 260/465 D; 424/304, 308, 309

[56] References Cited

U.S. PATENT DOCUMENTS 4,277,617 7/1981 Martel ................................ 560/124

Primary Examiner—Michael L. Shippen
Attorney, Agent, or Firm—Cushman, Darby & Cushman

[57] ABSTRACT

The invention concerns novel pesticidal esters of the pyrethrin or pyrethroid type in which the methylene group bonded to the ester carbonyl and/or ester oxygen bears a fluorine substituent. The compounds of the invention are active against insect pests including flies, moths, aphids and beetles and acarina pests including ticks.

11 Claims, No Drawings

PESTICIDAL FLUORINATED ESTERS OF THE PYRETHRIN OR PYRETHROID TYPE

This is a division, of application Ser. No. 46,757 filed June 8, 1979 now U.S. Pat. No. 4,283,414.

This invention relates to pesticides, and more particularly to fluorinated ester derivatives useful as pesticides, to processes for the preparation of the derivatives, to compositions comprising the derivatives and to methods of combatting pests using the derivatives.

We have now found that certain novel ester derivatives which contain a fluoro substituted methylene group α- to the ester carbonyl and/or α- to the ester oxygen are active against pests such as insects and acarina.

Accordingly the invention provides an ester of the formula I

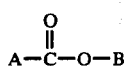

wherein

is a pyrethrin acid moiety or a pyrethroid type acid moiety and B—O— is a pyrethrin alcohol moiety or a pyrethroid type alcohol moiety; and wherein A comprises a fluoro-substituted methylene moiety directly bonded to the ester carbonyl group and/or B comprises a fluoro-substituted methylene moiety directly bonded to the oxygen atom of the ester.

In a preferred aspect the invention provides an ester of the formula I

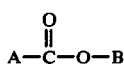

wherein A is chosen from the group consisting of the formulae

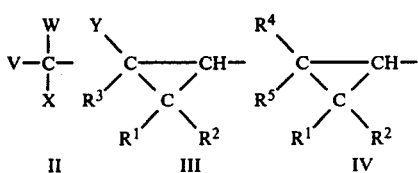

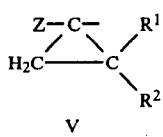

wherein V represents a substituted aromatic group or an unsaturated alicyclic group or an alkenyl group and is selected from the group consisting of the formulae

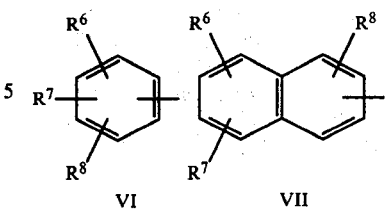

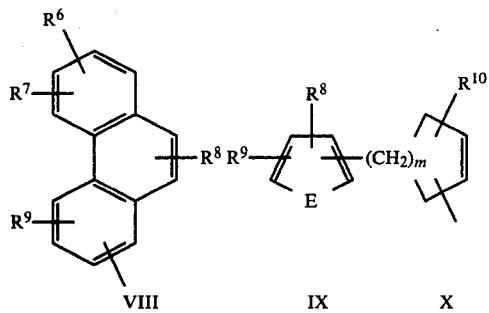

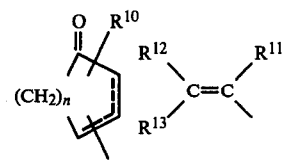

in which $R^6$ and $R^7$ are independently chosen from hydrogen, halogen, cyano, nitro, $C_1$ to $C_6$ alkyl optionally substituted with halogen atoms or $C_1$ to $C_6$ alkoxy, $C_2$ to $C_6$ alkenyl optionally substituted with halogen atoms, $C_2$ to $C_6$ alkynyl optionally substituted with halogen atoms, $C_1$ to $C_6$ alkoxy, $C_1$ to $C_6$ alkylthio, $C_1$ to $C_6$ alkylsulfinyl, acyl, acyloxy, $C_1$ to $C_6$-(alkoxy)carbonyl, $C_2$ to $C_6$-(alkenyloxy)carbonyl and $C_2$ to $C_6$-(alkynyloxy)carbonyl, or $R^6$ and $R^7$ may jointly form a methylene dioxy, tetramethylene or trimethylene group; $R^8$ and $R^9$ are independently chosen from hydrogen, halogen, cyano, nitro, $C_1$ to $C_6$ alkyl optionally substituted with halogen atoms or $C_1$ to $C_6$ alkoxy, $C_2$ to $C_6$ alkenyl optionally substituted with halogen atoms, $C_2$ to $C_6$ alkynyl optionally substituted with halogen atoms, $C_1$ to $C_6$ alkoxy, $C_1$ to $C_6$ alkylthio, $C_1$ to $C_6$ alkylsulfinyl, acyl, acyloxy, $C_1$ to $C_6$-(alkoxy)carbonyl, $C_2$ to $C_6$-(alkenyloxy)carbonyl and $C_2$ to $C_6$-(alkynyloxy)carbonyl; E represents an oxygen atom or a sulfur atom; $R^{10}$ is chosen from hydrogen, halogen, cyano, nitro and $C_1$ to $C_6$ alkyl; m and n are independently integers of from 1 to 3; the dotted line in formula XI represents a double bond present at a position either conjugated with or non-conjugated with the ketone group (C=O); $R^{11}$, $R^{12}$ and $R^{13}$ are independently chosen from hydrogen, $C_1$ to $C_6$ alkyl, $C_2$ to $C_6$ alkenyl, $C_2$ to $C_6$ alkynyl, halogen, acyl and acyloxy;

W represents a straight or branched chain $C_1$ to $C_6$ alkyl group optionally substituted with halogen, a straight or branched chain $C_2$ to $C_6$ alkenyl group optionally substituted with halogen, a straight or branched chain $C_2$ to $C_6$ alkynyl group $C_1$ to $C_6$ alkoxy, cyano or a $C_3$ to $C_7$ alicyclic group;

X is hydrogen or fluorine;

Y is the group $R^{15}R^{16}C=CR^{14}$ in which $R^{14}$ is hydrogen or $C_1$ to $C_6$ alkyl; $R^{15}$ is hydrogen, halogen or $C_1$ to $C_6$ alkyl optionally substituted with halogen atoms; $R^{16}$ is chosen from the group consisting of hydrogen, halogen, $C_1$ to $C_6$ alkyl optionally substituted with halogen atoms, $C_1$ to $C_6$ alkyl substituted with $C_1$ to $C_6$ alkoxy, $C_1$ to $C_6$ alkyl substituted with $C_2$ to $C_6$ alkenyloxy, $C_1$ to $C_6$ alkyl substituted with $C_2$ to $C_6$ alkynyloxy, $C_1$ to $C_6$-(alkoxy)carbonyl, acyl, a substituent of the formula $R^{18}R^{19}C\!=\!CR^{17}-$ wherein $R^{17}$, $R^{18}$ and $R^{19}$ are individually hydrogen or $C_1$ to $C_6$ alkyl, and a substituent of the formula $R^{20}ON\!=\!CH-$ wherein $R^{20}$ is hydrogen or $C_1$ to $C_6$ alkyl or $C_2$ to $C_6$ alkenyl or $C_2$ to $C_6$ alkynyl; or $R^{15}$ and $R^{16}$ jointly may form a cycle of formula

   XIII wherein
G is

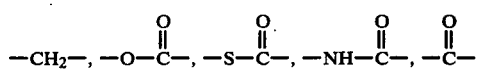

and p is an integer of from 2 to 5;

$R^3$ is hydrogen or $C_1$ to $C_6$ alkyl;

$R^1$ and $R^2$ are independently chosen from hydrogen, halogen and $C_1$ to $C_6$ alkyl, or $R^1$ and $R^2$ jointly form an ethylene, trimethylene, tetramethylene or pentamethylene bridging group;

$R^4$ and $R^5$ are independently chosen from hydrogen, $C_1$ to $C_6$ alkyl, halogen and phenyl optionally substituted with one or more groups or atoms chosen from halogen, nitro, cyano, $C_1$ to $C_6$ alkyl, $C_1$ to $C_6$ haloalkyl and $C_1$ to $C_6$ alkoxy or $R^4$ and $R^5$ jointly form a bridging group selected from ethylene, trimethylene, tetramethylene, pentamethylene and groups of the formulae

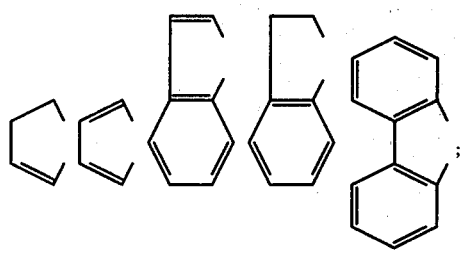

XIV   XV   XVI   XVII   XVIII

Z is selected from $C_1$ to $C_6$ alkyl, $C_2$ to $C_6$ alkenyl, $C_2$ to $C_6$ alkynyl and the group

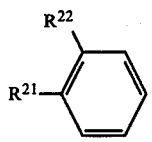   XIX in which $R^{21}$ is chosen from hydrogen, $C_1$ to $C_3$ alkoxy, $C_1$ to $C_3$ alkylthio, $C_1$ to $C_2$ alkyl, nitro, fluoro, chloro, bromo and amino; $R^{22}$ is chosen from hydrogen and methyl; or $R^{21}$ and $R^{22}$ jointly is a methylenedioxy bridging group; B represents a group corresponding to an alcohol moiety of the ester-type insecticides which are known as pyrethroid and pyrethroid-like insecticides, and is chosen from the group consisting of the formulae

   XX

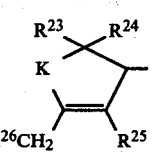   XXI

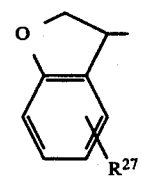   XXII wherein Q represents an alkenyl, alkynyl, aryl or heteroaryl group and is selected from the group consisting of the formulae

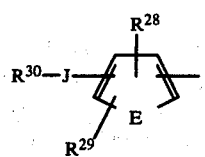   XXIII

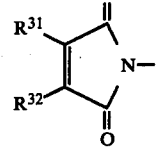   XXIV

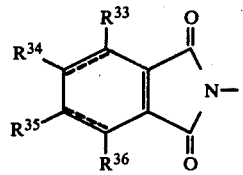   XXV

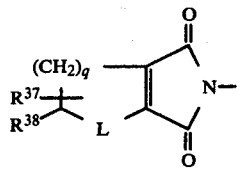   XXVI

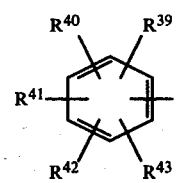   XXVII

-continued

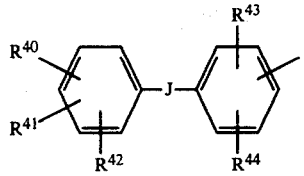
XXVIII

XXIX

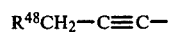
XXX in which $R^{28}$ and $R^{29}$ are independently selected from hydrogen, halogen, $C_1$ to $C_6$ alkyl optionally substituted with halogen atoms, or $R^{28}$ and $R^{29}$ may jointly form a trimethylene or tetramethylene bridging group; J is chosen from oxygen, sulfur

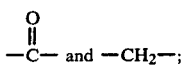

$R^{30}$ is chosen from hydrogen, $C_1$ to $C_6$ alkyl, $C_2$ to $C_6$ alkenyl, $C_2$ to $C_6$ alkynyl and the groups phenyl, furyl, and thienyl each group being optionally substituted by halogen, $C_1$ to $C_6$ alkyl, $C_1$ to $C_6$ alkoxy or $C_2$ to $C_6$ alkenyl; E is chosen from oxygen and sulfur; $R^{31}$ and $R^{32}$ are independently chosen from $C_1$ to $C_6$ alkyl; $R^{33}$, $R^{34}$, $R^{35}$ and $R^{36}$ are independently chosen from hydrogen, halogen and $C_1$ to $C_6$ alkyl; the dotted lines in formula XXV represent optional double bonds; $R^{37}$ and $R^{38}$ are independently chosen from hydrogen, $C_1$ to $C_6$ alkyl, halogen or $R^{37}$ and $R^{38}$ jointly form a methylenedioxy bridging group; L is chosen from oxygen, sulfur and —CH$_2$—; q is an integer of from 1 to 2; $R^{39}$ is chosen from hydrogen, $C_1$ to $C_6$ alkyl, $C_2$ to $C_6$ alkenyl, $C_2$ to $C_6$ alkynyl, thienyloxy, thenyl, furylmethyl and the groups $R^{50}R^{51}C=C(R^{49})O-$ and $R^{50}R^{51}C=C(R^{49})-$ in which $R^{49}$ is hydrogen or $C_1$ to $C_6$ alkyl and $R^{50}$ and $R^{51}$ are independently chosen from hydrogen, halogen and $C_1$ to $C_6$ alkyl optionally substituted with halogen atoms; $R^{40}$, $R^{41}$, $R^{42}$, $R^{43}$ and $R^{44}$ are independently chosen from hydrogen, $C_1$ to $C_6$ alkyl, halogen and $C_2$ to $C_6$ alkenyl; J is chosen from oxygen, sulfur,

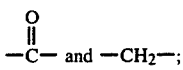

$R^{45}$ is chosen from hydrogen, chlorine, and $C_1$ to $C_6$ alkyl; $R^{46}$ and $R^{47}$ are independently chosen from, hydrogen, fluorine, chlorine, bromine, $C_1$ to $C_6$ alkyl, $C_2$ to $C_6$ alkenyl, $C_2$ to $C_6$ alkynyl, phenyl, benzyl, furylmethyl and thienylmethyl; and $R^{48}$ is chosen from the groups phenyl and phenoxy both optionally substituted with one or more groups or atoms chosen from halogen, nitro, cyano, $C_1$ to $C_6$ alkyl, $C_1$ to $C_6$ haloalkyl and $C_1$ to $C_6$ alkoxy;

X is hydrogen or fluorine;

T is chosen from hydrogen, halogen, cyano, thiocarbamoyl, $C_1$ to $C_6$ alkyl optionally substituted with halogen, $C_1$ to $C_6$ alkoxy, $C_1$ to $C_6$ alkylthio, $C_2$ to $C_6$ alkenyl and $C_2$ to $C_6$ alkynyl;

K is

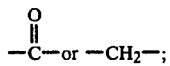

$R^{23}$, $R^{24}$ and $R^{25}$ are independently chosen from hydrogen and $C_1$ to $C_6$ alkyl;

$R^{26}$ is chosen from $C_2$ to $C_6$ alkenyl, $C_3$ to $C_6$ allyl, $C_4$ to $C_6$ alkadienyl and phenyl;

$R^{27}$ is chosen from hydrogen, halogen, nitro, $C_1$ to $C_6$ alkyl, $C_1$ to $C_6$ alkoxy, $C_1$ to $C_6$ alkylthio, $C_1$ to $C_6$ alkylsulfonyl, phenyl and benzyl;

and wherein A is a group of the formula II in which X is fluorine and/or B is a group of formula XX in which X is fluorine.

The term "pyrethrin" as used herein refers to the naturally occurring insecticidally active constituents of pyrethrum flowers including the chrysanthemates such as pyrethrin I, cinerin I and jasmolin I and the pyrethrates such as pyrethrin II, cinerin II and Jasmolin II. The term "pyrethroid" or "pyrethroid type" as used herein refers to those synthetic esters made to mimic the natural pyrethrins and including the cyclopropanecarboxylates and α-isopropylarylacetates some of which are discussed in the book "Synthetic Pyrethroids", ACS Synposium Series 42, Editor M Elliott, American Chemical Society, Washington D.C., 1977, and others which are the subject of the patents referred to below.

Examples of suitable pyrethroid type acid moieties

wherein A is a group of formula

(II) in which X is hydrogen and V and W are as hereinbefore defined include those described in Australian Pat. No. 475,379 and its foreign counterparts which are herein incorporated by reference. The group of formula

(II) in which X is hydrogen is represented in Australian Patent Specification No. 475,379 by the formula

wherein Y and Z are as defined in that specification.

Further examples of suitable pyrethroid type acid moieties

wherein A is a group of formula

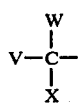

(II) in which X is hydrogen and V is naphthyl or substituted naphthyl include those described in U.S. Pat. Nos. 4,046,799 and 4,053,631, Belgium Pat. No. 855,518 and Japanese Patent Publication No. 52-091833 and their equivalents and these descriptions are herein incorporated by reference. Examples of suitable pyrethroid type acid moieties

wherein A is a group of formula

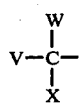

(II) in which X is hydrogen and V is phenanthryl or substituted phenanthryl are described in Japanese Patent Publication No. 52-070022 and its equivalents which are herein incorporated by reference.

Novel pyrethroid type acid moieties

wherein A is a group of formula

(II) include those acids herein incorporated by the preceding references wherein X is fluorine and V and W are as hereinbefore defined. Examples of suitable pyrethroid acid moieties

wherein A is a group of formula

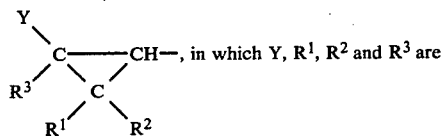

(III), in which Y, $R^1$, $R^2$ and $R^3$ are as hereinbefore defined, include the naturally occurring chrysanthemic acid and pyrethric acid moieties and analogous synthetic pyrethroid acid moieties described in Belgium Pat. Nos. 785,478, 770,874 and 840,419, German Patent Publication Nos. 2,230,862, 2,231,312 and 2,539,895, Japanese Patent Publication Nos. 49-080242 and 51-125739 French Patent Publication Nos. 2,232,273 and 2,281,613, Netherlands Patent Publication No. 75 13896, U.S. Pat. No. 3,987,193 and Australian Pat. No. 484,834 which are herein incorporated by reference.

Further examples of suitable pyrethroid acid moieties

wherein A is a group of formula

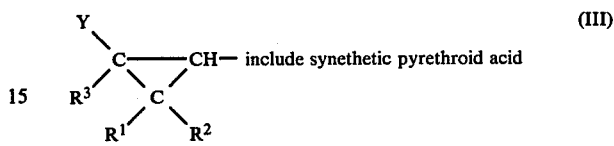

(III) include synthetic pyrethroid acid moieties in which $R^1$ and $R^2$ are methyl, $R^3$ is hydrogen and Y is the group $R^{15}R^{16}C{=}CR^{14}{-}$ in which $R^{14}$ is hydrogen, $R^{15}$ is a $C_1$ to $C_6$ alkyl group substituted by one or more halogen atoms and $R^{16}$ is chosen from halogen and $C_1$ to $C_6$ alkyl optionally substituted by one or more halogen atoms.

Examples of suitable pyrethroid type acid moieties

wherein A is a group of formula

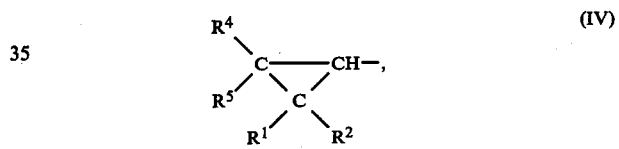

in which $R^1$, $R^2$, $R^4$ and $R^5$ are as hereinbefore defined, include the synthetic pyrethroid type acid moieties described in Belgium Pat. Nos. 814,819, 820,413, 846,544, 852,505 and 855,010, Japanese Patent Publication Nos. 50-071825 and 51-148024, West German Patent Publication Nos. 2,231,312, 2,407,024 and 2,713,651 and U.S. Pat. Nos. 3,986,959 and 4,045,469 which are herein incorporated by reference.

Examples of suitable pyrethroid type acid moieties

wherein A is a group of formula

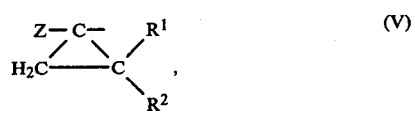

in which Z, $R^1$ and $R^2$ are as hereinbefore defined, include the synthetic pyrethroid type acid moieties described in Japanese Patent Publication No. 49-075725 and West German Patent Publication No. 2,653,189 which are herein incorporated by reference.

Suitable alcohol moieties include the natural pyrethrin alcohols and synthetic (pyrethroid type) alcohols.

Examples of suitable pyrethroid type alcohol moieties B—O— wherein B is a group of formula

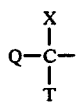
(XX), in which X is hydrogen and Q and T are as hereinbefore defined, include those described in Australian Pat. Nos. 484,834 and 475,379 and their foreign counterparts, West German Patent Publication Nos. 2,554,883, 2,547,534, 2,647,366 and 2,719,561, Japanese Patent Publication Nos. 49-125523, 50-071828 and 51-125739 and Belgium Pat. No. 842,061 which are herein incorporated by reference.

Suitable novel pyrethroid type alcohol moieties B—O— wherein B is a group of formula

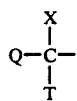
(XX) include those alcohols herein incorporated by the references in the preceding paragraph wherein X is fluorine and Q and T are as hereinbefore defined.

Examples of suitable pyrethroid type alcohol moieties B—O— wherein B is a group of formula

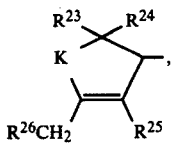 (XXI)

wherein K, $R^{23}$, $R^{24}$, $R^{25}$ and $R^{26}$ are as hereinbefore defined, include those described in Japanese Patent Publication No. 51-125739 which is herein incorporated by reference.

Examples of suitable pyrethroid type alcohol moieties B—O— wherein B is a group of formula

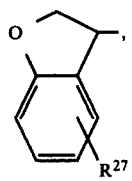 XXII wherein $R^{27}$ is as hereinbefore defined, include those described in U.S. Pat. No. 4,053,629 which is herein incorporated by reference.

More preferred compounds of the invention are those compounds of general formula I wherein:
(i) A is chosen from the groups given in Table 1 below in which X is a hydrogen atom, or Table 2 below and B is chosen from the groups given in Table 3 below in which X is a fluorine atom;
(ii) A is chosen from the group given in Table 1 below in which X is a fluorine atom, and B is chosen from the groups given in Table 3 below wherein X is a hydrogen atom, or Table 4 below; or
(iii) A is chosen from the groups given in Table 1 below in which X is a fluorine atom and B is chosen from the groups given in Table 3 below in which X is a fluorine atom.

TABLE 1

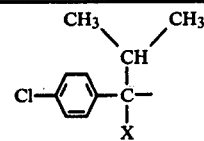

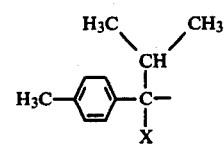

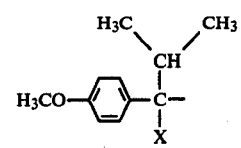

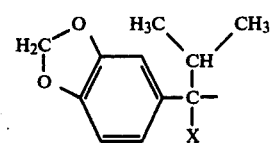

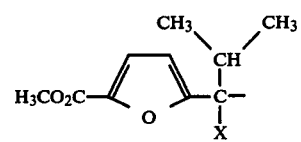

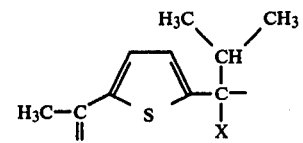

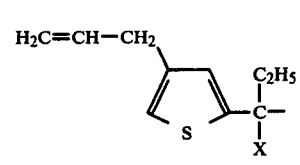

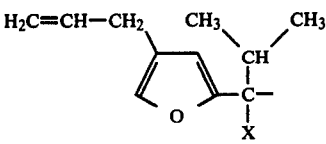

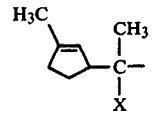

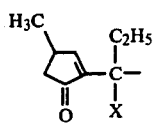

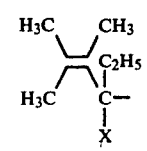

TABLE 1-continued
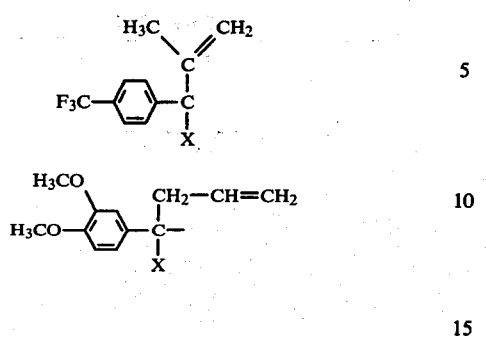
TABLE 1-continued
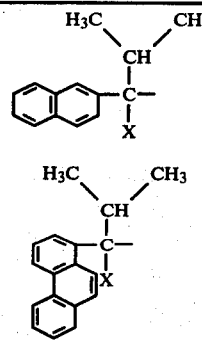
TABLE 2
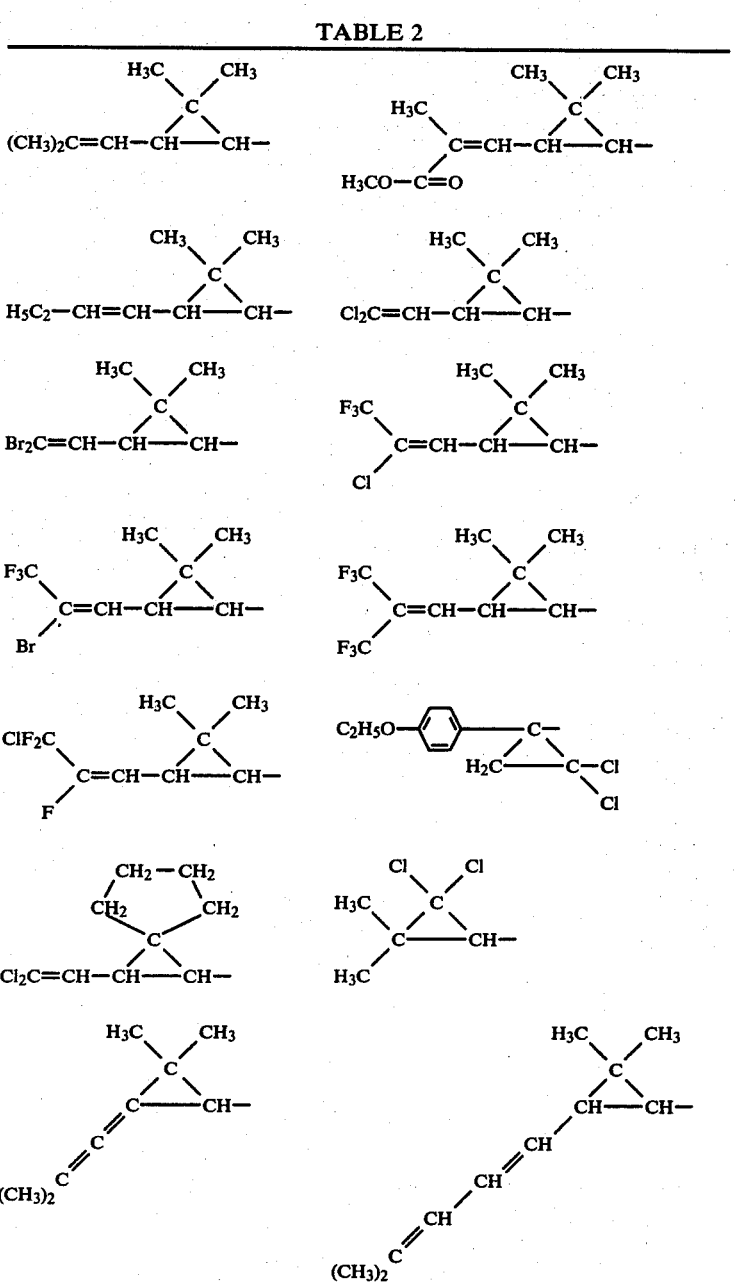

TABLE 2-continued
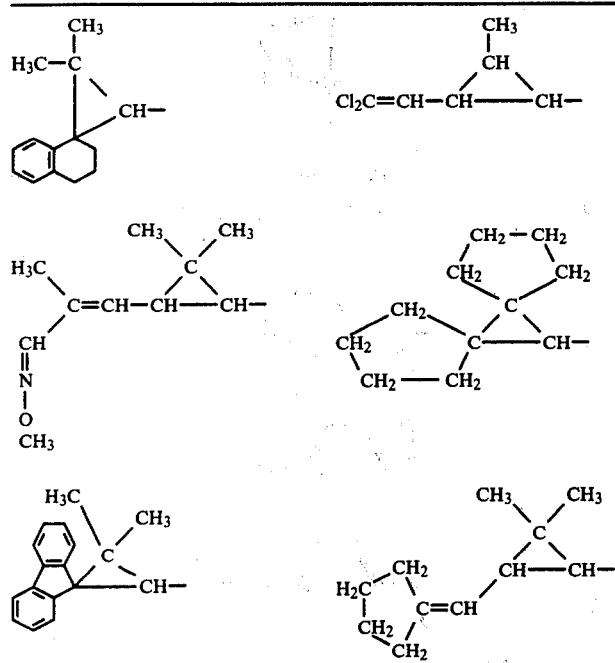
TABLE 3
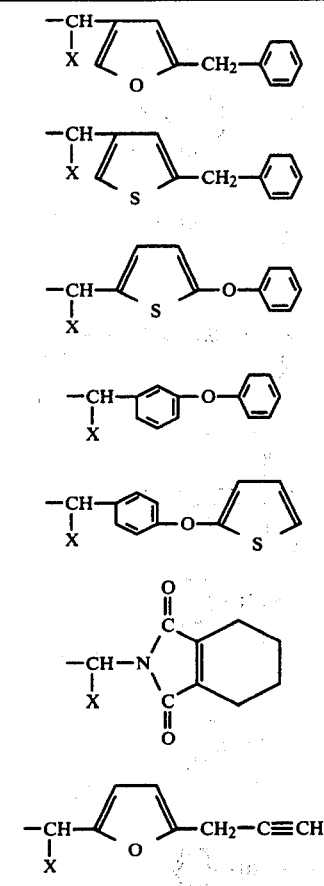
TABLE 3-continued
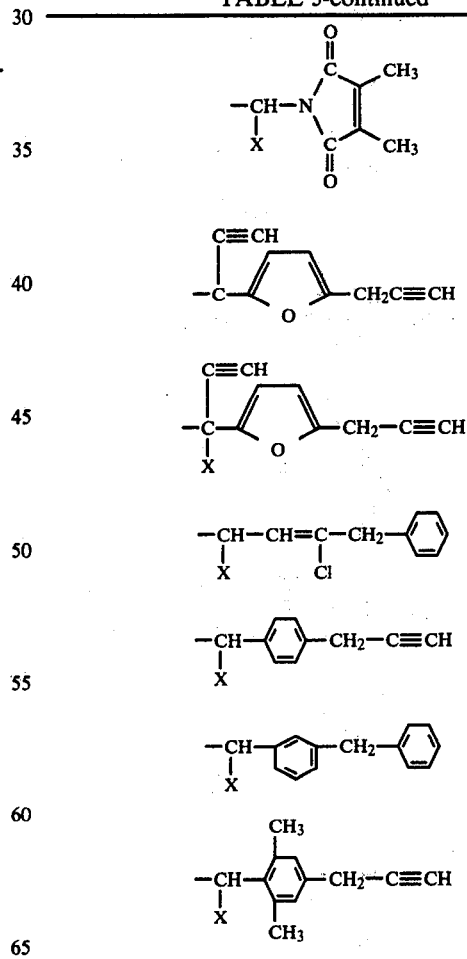

TABLE 3-continued
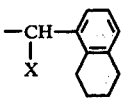
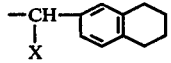
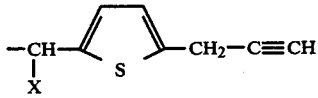
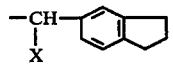
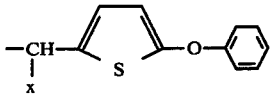
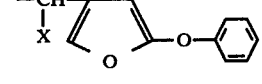
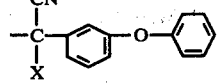
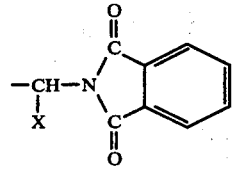
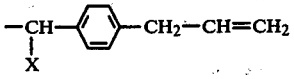
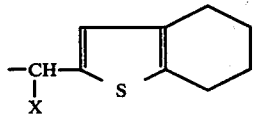
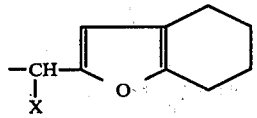
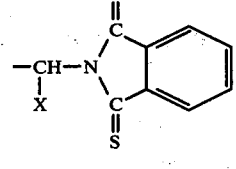
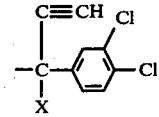
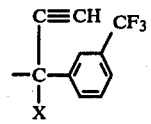
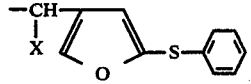
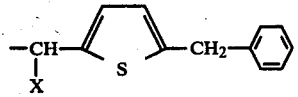
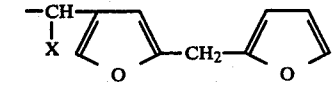
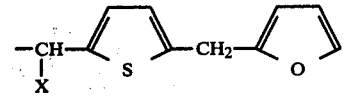
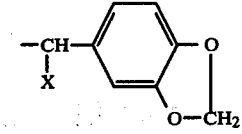
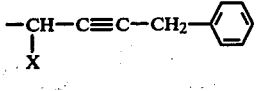
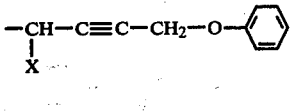
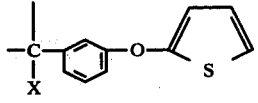
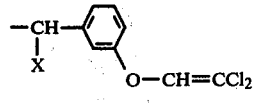
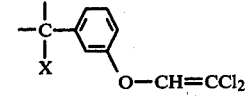
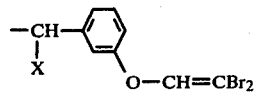

TABLE 3-continued
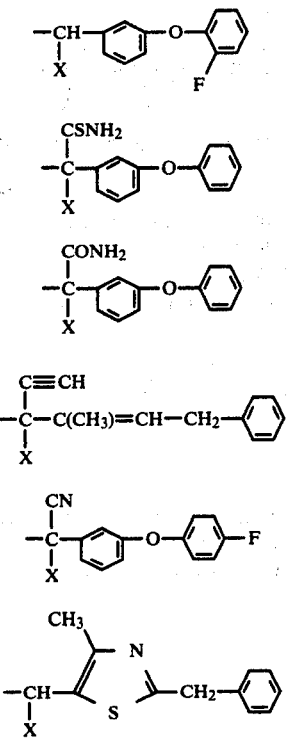
TABLE 4
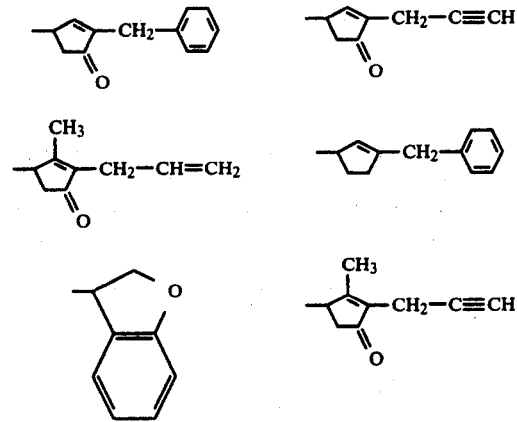
Representative examples of the compounds of the invention are illustrated in Table 5.
TABLE 5
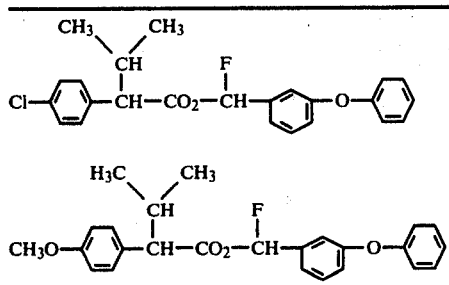
TABLE 5-continued
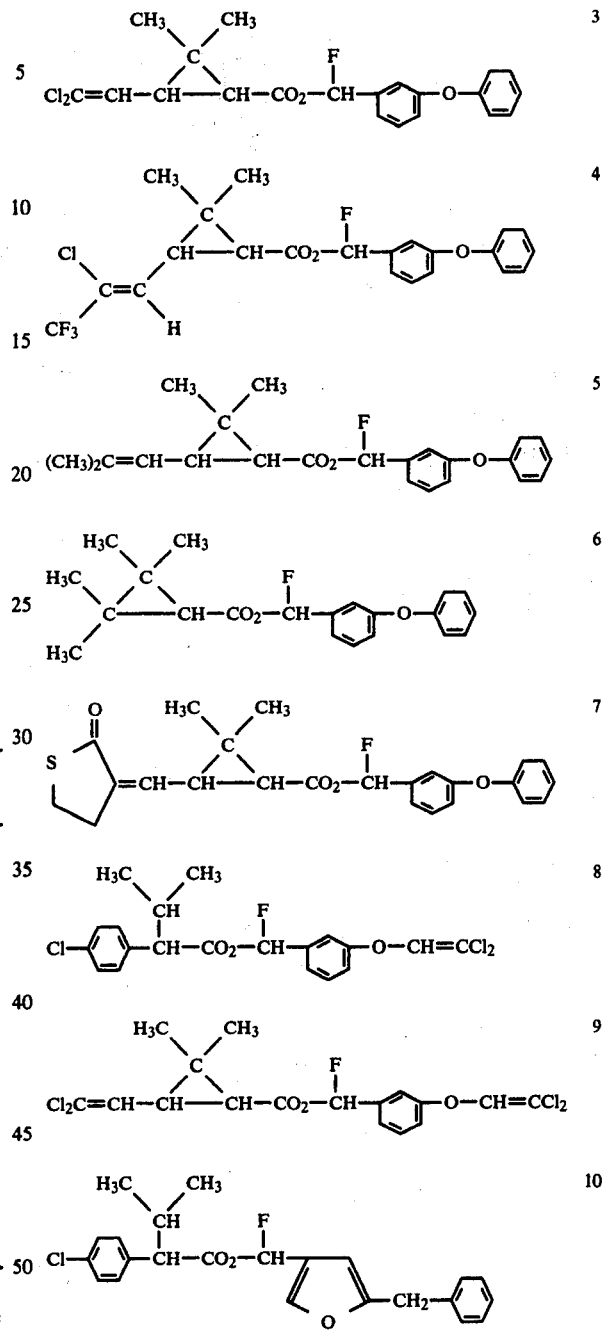
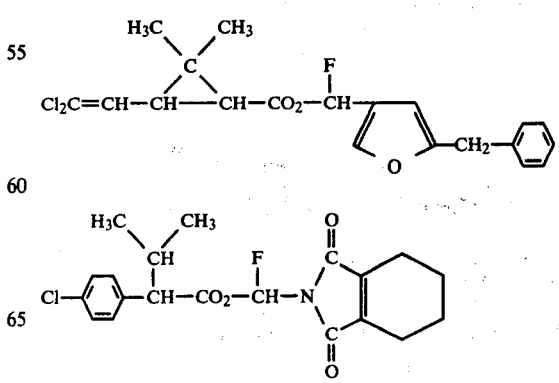

TABLE 5-continued

| | |
|---|---|
| 13 | 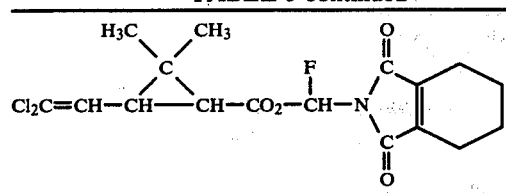 |
| 14 | 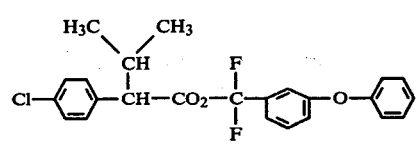 |
| 15 | 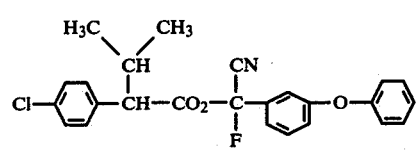 |
| 16 | 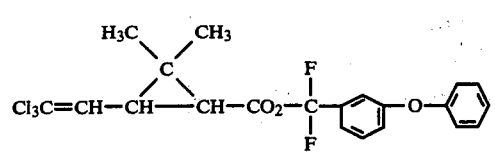 |
| 17 | 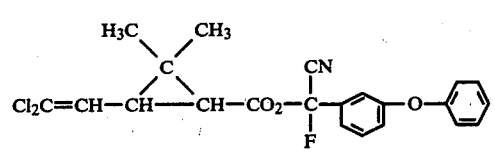 |
| 18 | 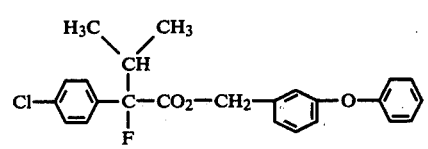 |
| 19 | 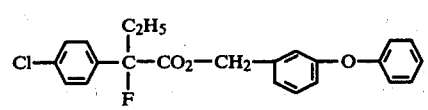 |
| 20 | 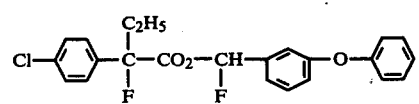 |
| 21 | 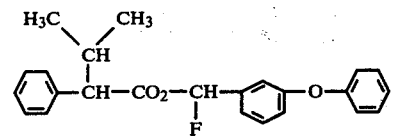 |
| 22 | 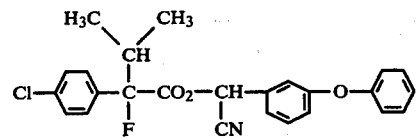 |
| 24 | 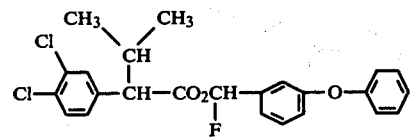 |

TABLE 5-continued

| | |
|---|---|
| 25 | 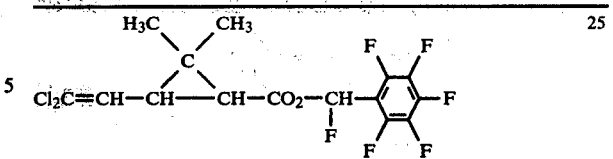 |

It will be evident to those skilled in the art that the compounds of the invention are capable of existing in the form of various stereoisomers and/or geometrical isomers. For example:

(i) compounds of formula I wherein A is a group of formula

(II) can exist in two stereoisomeric forms when W and X are different;

(ii) compounds of formula I wherein A is a group of formula

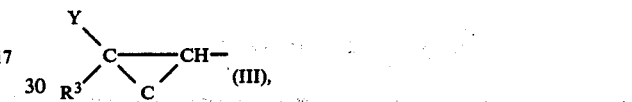

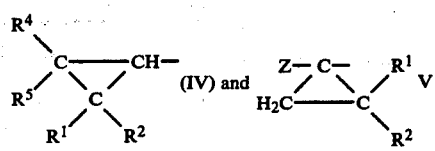

can exist in the form of cis- and trans-geometrical isomers arising from the substitution pattern of the cyclopropane ring and stereoisomers arising from asymmetrical substitution of the cyclopropane ring;

(iii) in compounds of formula I wherein A is a group of formula

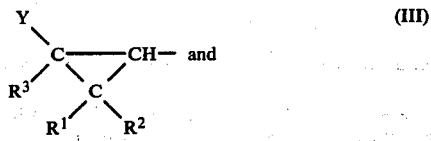

(III) and
Y is the group $R^{15}R^{16}C=CR^{14}$ cis- and trans-isomers arise from the vinyl group when $R^{15}$ is not the same as $R^{16}$; and (iv) compounds of formula I wherein B is a group of formula

(XX) can exist in two stereoisomeric forms when T and X are different. As a result it is to be understood that this invention embraces the various geometrical isomers and stereoisomers of the compounds of formula I.

The compounds of the invention according to formula I are esters and may be prepared by conventional esterification processes. For example (i) Reaction of an acid of formula

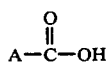

with an alcohol of formula B-OH, wherein A and B are as hereinbefore defined, the reaction preferably taking place in the presence of an acid catalyst such as dry hydrogen chloride.

(ii) Reaction of an acid halide of formula

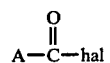

with an alcohol of formula B-OH, wherein A and B are as hereinbefore defined and hal represents a halogen atom, preferably a chlorine atom, the reaction preferably taking place in the presence of a base such as pyridine, alkali metal hydroxide, alkali metal carbonate or alkali metal alkoxide.

(iii) Reaction of an acid of formula

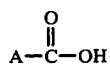

with a halide of formula B-hal, wherein A and B are as hereinbefore defined and hal represents a halogen atom, preferably a chlorine or a bromine atom.

(iv) Reaction of a lower alkyl ester of formula

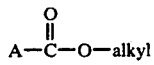

with an alcohol of formula B—OH, wherein A and B are as hereinbefore defined and alkyl is a $C_1$ to $C_6$ alkyl group, to effect a transesterification reaction the reaction preferably taking place in the presence of a suitable catalyst such as an alkali metal hydroxide or alkylated titanium derivative.

All of these conventional processes for the preparation of esters may be carried out using solvents and/or diluents for the various reactants where appropriate and may be accelerated or give higher yields of product when performed at elevated temperatures or in the presence of appropriate catalysts such as, for example, phase transfer catalysts.

The preparation of individual isomers may be carried out in the same manner but starting from the corresponding individual isomers of the acid of formula

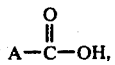

the acid halide of formula

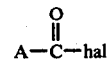

or the acid ester of formula

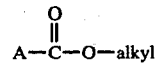

wherein A, hal and alkyl have the meanings defined above. These individual isomers may be obtained by conventional isomer separation techniques from mixtures of isomers. Thus cis- and trans-isomers may be separated by fractional crystallisation of the carboxylic acids or salts thereof, whilst the various optically active species may be obtained by fractional crystallisation of salts of the acids with optically active amines followed by regeneration of the optically pure acid.

The optically pure isomeric form of the acid (or its equivalent acid chloride or ester) may then be reacted with the alcohol (B—OH) or alkyl halide (B-hal) to produce the compounds of formula I in the form of an individually pure isomer thereof. In the case of alcohols (B—OH) or alkyl halides (B-hal) wherein B is a group of the formula

(XX) in which T and X are different the product will be a mixture of two isomers since the alcohol or halide will racemise during the esterification reaction.

The various acids

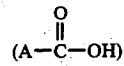

acid halides

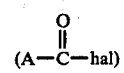

and acid esters

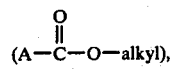

wherein A is a group of the formula

(II), hal is a hydrogen atom, alkyl is a $C_1$ to $C_6$ alkyl group, X is fluorine and V and W are as hereinbefore defined, which are useful intermediates in the preparation of the invention compounds of formula I are in themselves novel compounds.

In a further aspect therefore the present invention provides compounds according to the formula XXXI

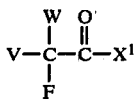 XXXI wherein V and W have any of the meanings hereinbefore defined and $X^1$ is chosen from hydroxy, chlorine, bromine and $C_1$ to $C_6$ alkoxy.

The acids and acid derivatives of formula XXXI may be prepared from the acetic acid derivatives of formula

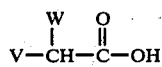

by bromination and halogen exchange to replace bromine by fluorine. Alternatively the acid or acid derivatives of formula XXXI may be prepared from the acetic acid derivative of formula

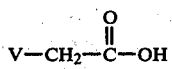

by bromination and halogen exchange as indicated above followed by the introduction of the substituent group W.

The various alcohols (B—OH) and alkyl halides (B-hal) wherein B is a group of the formula

 XX hal is a halogen atom, X is fluorine and Q and T are as hereinbefore defined, which are useful in the preparation of the invention compounds of formula I are in themselves novel compounds.

Accordingly in another aspect the invention provides compounds of the formula XXXII

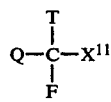 XXXII wherein Q and T have any of the meanings hereinbefore defined and $X^{11}$ is chosen from hydroxy, chlorine, and bromine.

The alkyl halides of formula XXXII may be prepared from the corresponding alcohols of formula

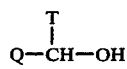

by reaction with 2-chloro-1-diethylamino-1,1,2-trifluoroethane to replace the hydroxyl group by fluorine followed by chlorination or bromination to give the alkyl halide of formula XXXII. Alternatively the alkyl halides of formula XXXII may be prepared from the corresponding alkyl halides of formula

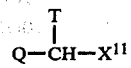

by halogen exchange to replace the bromine or chlorine atom $X^{11}$ with a fluorine atom followed by chlorination or bromination to give the alkyl halide of the formula XXXII. The alcohols of formula XXXII may be prepared from the alkyl halides of formula XXXII by conventional processes.

The compounds of formula I may be used to combat and control infestations of insect pests and also other invertebrate pests, for example, acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise an insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example, cetyltrimethyl ammonium bromide. Suitable agents of the anionic type include, for example, soaps, salts of aliphatic monoesters or sulphuric acid, for example sodium lauryl sulphate, salts or sulphonated aromatic compounds, for example sodium dodecylbenzenesulphonate, sodium, calcium or ammonium lignosulphonate, butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydro furfuryl alcohol (THFA).

The compositions to be used as sprays may also be in the form of aerosols wherein the formulation is held in a container under pressure in the presence of a propellant such as fluorotrichloromethane or dichlorodifluoromethane. The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations, such preparations may contain varying amounts of the active ingredient depending upon the purpose of which they are to be used.

For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:
*Aphis fabae* (aphids)
*Megoura viceae* (aphids)
*Musca domestica* (houseflies)
*Phaedon cochleariae* (mustard beetle)
*Spodoptera littoralis* (cotton leaf worm)
*Sitophilus granarius* (grain weevil)
*Plutella xylostella* (diamond back cabbage moth)
*Aphis craccivora* (cowpea aphid)
Boophilus spp.
Ixodes spp.
Hyalomma spp.
Amblyomma spp.
Rhipicephalus spp.
Dermaceutor spp.
Lucilia spp.

The compounds of formula I and compositions comprising them are particularly useful in controlling the housefly (*Musca domestica*) the larvae of the diamond back cabbage moth (*Plutella xylostella*), the mustard beetle (*Phaedon cochleariae*), and aphids (*Aphis fabae, Megoura viciae* and *Aphis craccivora*). In certain applications the compounds of the invention show pest repellent activity as well as pesticidal activity.

Where the compounds of the invention are used to combat animal pests the compounds, in addition to application in the form of a spray, dip or dusting powder, may be applied in the form of a "pour-on" or incorporated in shaped solid articles in the form of bands, collars, ear tags and tail tags. For certain applications the compounds of the invention may be administered to the animals orally in the form of a drench or by incorporation into the animals' feed to systemically combat the insect pests.

The invention is now illustrated by, but by no means limited to, the following Examples.

EXAMPLE 1 α-FLUORO-3-PHENOXYBENZYL BROMIDE

Preparation of 3-Phenoxybenzyl Fluoride

Method A

3-Phenoxybenzyl chloride (4.37 g), potassium fluoride (5.8 g), tri-n-butylhexadecylphosphonium bromide (1.2 g) and water (10 ml) were stirred for a period of 8 hours in a pressure bottle heated at a temperature of 130° C. The oil was separated and the aqueous phase was diluted with water and extracted with ethylene dichloride. The oil and ethylene dichloride extract were combined and the phosphonium salt was removed by chromatography over silica gel (15 g). The eluate was concentrated and distilled to give 3-phenoxybenzyl fluoride (1.96 g; 49%) b.p. 92°–95° C. at 0.3 mm Hg. (The product was stabilized by the addition of a small amount of anhydrous calcium carbonate to prevent acid catalysed polymerization).

METHOD B

3-Phenoxybenzyl alcohol (5.2 g) and methylene dichloride (90 ml) were cooled to a temperature of 0° C. in an ice-bath and 2-chloro-1-diethylamino-1,1,2-trifluoroethane (7.0 g) was slowly added to the cooled, stirred mixture over a period of ten minutes. The reaction mixture was stored overnight at a temperature of 5° C.

The mixture was washed with aqueous potassium carbonate solution and then with water and the organic layer was dried over anhydrous sodium sulfate. The solvent was removed by distillation under reduced pressure and the product was chromatographed over silica gel using 10% ethylene dichloride in petroleum ether as eluant. The eluant was removed by distillation under reduced pressure to give 3-phenoxybenzyl fluoride (1.78 g; 34%).

A mixture of 3-phenoxybenzyl fluoride (5.07 g), N-bromosuccinimide (4.68 g) and carbon tetrachloride (150 ml) was stirred and heated under reflux for a period of 5.5 hours while being illuminated by a 400 W infrared lamp. The succinimide formed was removed by filtration and the filtrate concentrated by distillation under reduced pressure. The product was distilled under reduced pressure to give α-fluoro-3-phenoxybenzyl bromide (4.48 g; 53%) b.p. 119°–122° C. at 0.4 mm Hg.

EXAMPLE 2 α-FLUORO-3-PHENOXYBENZYL α-ISOPROPYL-4-CHLOROPHENYLACETATE (1)

METHOD A

α-Isopropyl-4-chlorophenylacetic acid (1.3 g) was dissolved in ethanol (10 ml) and a solution of potassium hydroxide (0.34 g) in water (5 ml) was added to the ethanolic solution. The solvents were then removed by distillation under reduced pressure to give anhydrous potassium α-isopropyl-4-chlorophenylacetate.

A mixture of potassium α-isopropyl-4-chlorophenylacetate (0.91 g) and α-fluoro-3-phenoxy benzyl bromide (1.06 g) in dimethylformamide (10 ml) was stirred at ambient temperature over a period of 2 hours. The reaction mixture was poured into water and the aqueous solution was extracted with diethyl ether. The ether extract was washed with aqueous sodium carbonate solution and was then dried over anhydrous sodium sulfate. The ether was removed by distillation under reduced pressure and the residue chromatographed over silica gel to give α-fluoro-3-phenoxybenzyl α-isopropyl-4-chlorophenylacetate (0.62 g; 37%) as a colourless oil. The product was characterised by pmr spectroscopy. Chemical shift δppm (solvent CDCl$_3$): 0.69(3H,d,J=6 Hz, CH$_3$); 1.05(3H,d of d, J=6 Hz and J=2 Hz, CH$_3$); 2.34(1H, m, —CH(CH$_3$)$_2$); 3.29 (1H, d, J=10 Hz, CH); 7.22(1H, d of d, J=56 Hz and J=2 Hz, CHF) and c. 7.24(13H, m, aromatic protons).

METHOD B

A mixture of α-isopropyl-4-chlorophenylacetic acid (1.05 g), α-fluoro-3-phenoxybenzyl bromide (1.16 g), triethylamine (0.64 g) and acetone (6 ml) was heated under reflux with stirring for a period of 2 hours. Triethylamine hydrobromide was removed from the reaction mixture by filtration and the solvent was removed by distillation under reduced pressure. The product was dissolved in ethylene dichloride and the solution was washed in a sequence with 2 N HCl, water, 1 N NaOH and water. The ethylene dichloride solution was dried over anhydrous sodium sulfate and the solvent was removed by distillation under reduced pressure to yield α'-fluoro-3'-phenoxybenzyl α-isopropyl-4-chlorophenylacetate (1.61 g; 87%) as a colourless oil. The product was characterised by pmr spectroscopy (see Method A above).

EXAMPLE 3 α-FLUORO-3-PHENOXYBENZYL 2,2-DIMETHYL-3-(β,β-DICHLOROVINYL)CYCLOPROPANE-1-CARBOXYLATE (3)

2,2-Dimethyl-3-(β,β-dichlorovinyl)cyclopropane-1-carboxylic acid (1.0 g of ±42% cis- 58% trans-form), α-fluoro-3-phenoxybenzyl bromide (1.17 g), and triethylamine (0.64 g) were dissolved in acetone (6 ml) and the stirred mixture was heated under reflux for a period of 2 hours. Triethylamine hydrobromide was removed from the reaction mixture by filtration and the solvent was removed by distillation under reduced pressure. The product was dissolved in ethylene dichloride and the solution was washed in sequence with 2 N HCl, water, 1 N NaOH and water. The ethylene dichloride solution was dried over anhydrous sodium sulfate and the solvent was removed by distillation under reduced pressure to give α-fluoro-3-phenoxybenzyl 2,2-dimethyl-3-(β,β-dichlorovinyl)cyclopropane-1-carboxylate (1.69 g; 87%) as a colourless oil. The product was characterised by pmr spectroscopy. Chemical shift δppm (solvent CDCl$_3$): 1.28(6H, m, C(CH$_3$)$_2$); 1.63–2.43 (2H, m, cyclopropyl ring protons); 5.61 and 6.23 (1H, 2xd, vinyl proton); 7.17 (1H, d of d J=56 Hz and J=2 Hz, CHF) and c. 7.26 (9H, m, aromatic protons).

EXAMPLE 4 α-FLUORO-α-ISOPROPYL-4-CHLOROPHENYLACETIC ACID

A mixture of 4-chlorophenylacetic acid (34 g) and red phosphorus (1.5 g) was stirred under an atmosphere of nitrogen and dry bromine (20 g) was carefully added over a period of 30 minutes. The reaction mixture was heated to a temperature of 100° C. and dry bromine (32 g) was carefully added over a period of 45 minutes. The mixture was then heated under reflux for 3 hours and cooled. Ethyl alcohol (100 ml) was added to the reaction mixture and the mixture allowed to stand overnight. The ethanolic mixture was diluted with water and extracted with ethylene dichloride. The extract was washed with aqueous sodium carbonate, dried over anhydrous sodium sulfate and the solvent removed by distillation under reduced pressure. The product was distilled through a Fenske ring column to give ethyl α-bromo-4-chlorophenylacetate (33.4 g; 65%) b.p. 119° C. at 0.9 mm of Hg.

A mixture of ethyl α-bromo-4-chlorophenylacetate (37.3 g), anhydrous potassium fluoride (9.7 g) and dry dimethylformamide (75 ml) was heated with stirring at a temperature of 140°–150° C. for a period of 6 hours. The reaction mixture was poured into water and the aqueous mixture extracted with methylene dichloride. The organic extract was washed with aqueous sodium carbonate, dried over anhydrous sodium sulfate and the solvent was removed by distillation under reduced pressure. The product was distilled using a spinning band column to give ethyl α-fluoro-4-chlorophenylacetate (7.5 g; 29%) b.p. 67° C. at 0.06 mm Hg.

A mixture of ethyl α-fluoro-4-chlorophenylacetate (2.3 g), isopropyl bromide (1.10 g), sodium hydride (0.56 g of a 50% mixture in oil), dry hexamethylphosphoramide (6 ml) and dry benzene (6 ml) was heated with stirring at a temperature of 35° C. under nitrogen for a period of 22 hours. The reaction mixture was poured into ice-water and the aqueous mixture extracted with methylene chloride. The methylene chloride extract was dried over anhydrous sodium sulfate and solvent removed by distillation under reduced pressure. The product was chromatographed over silica gel using 15% ethylene dichloride in petroleum ether as eluant to give ethyl α-fluoro-α-isopropyl-4-chlorophenylacetate (1.42 g; 62%).

A mixture of ethyl α-fluoro-α-isopropyl-4-chlorophenylacetate (1.42 g) and potassium hydroxide (0.35 g) in methanol (5 ml) was stirred at ambient temperature for 2.5 hours. The reaction mixture was acidified with hydrochloric acid, diluted with water and the aqueous mixture extracted with methylene chloride. The methylene chloride extract was dried over anhydrous sodium sulfate and the solvent removed by distillation under reduced pressure to give α-fluoro-α-isopropyl-4-chlorophenylacetic acid (1.10 g; 87%) m.p. 120° C.

EXAMPLE 5 3-PHENOXYBENZYL α-FLUORO-α-ISOPROPYL-4-CHLOROPHENYLACETATE (18)

A solution of α-fluoro-α-isopropyl-4-chlorophenylacetic acid (0.23 g) in ethylene dichloride (4 ml) was treated with thionyl chloride (0.15 g) and the mixture was heated under reflux for a period of 2 hours. The solvent and excess thionyl chloride were removed from the mixture by distillation under reduced pressure and the product was treated with a mixture of 3-phenoxy benzyl alcohol (0.2 g), pyridine (0.09 g) and ethylene dichloride (3 ml). The mixture was stirred for a period of 2 hours at ambient temperature and then poured into water. The aqueous mixture was extracted with diethyl ether and the ether extract was washed in sequence with 2 N hydrochloric acid, water, 2 N sodium hydroxide and water. The ethereal solution was then dried over anhydrous sodium sulfate and the ether removed by distillation under reduced pressure pressure to give 3-phenoxybenzyl α-fluoro-α-isopropyl-4-chlorophenylacetate (0.41 g) as a colourless oil. The product was characterised by pmr spectroscopy. Chemical shift δppm (solvent CDCl₃): 0.71(3H, d, J=6.5 Hz, CH₃); 1.02(3H, d, J=6.5 Hz, CH₃); 2.6(1H, m, CH(CH₃)₂); 5.14 (2H, s, CH₂) and 6.75–7.55 (13H, m, aromatic protons).

EXAMPLE 6 3-PHENOXYBENZYL α-FLUORO-α-ISOPROPYLPHENYLACETATE (21)

This compound was prepared from 3-phenoxybenzyl bromide and α-fluoro-α-isopropylphenylacetic acid following the method used in Example 2 Method B for the preparation of α-fluoro-3-phenoxybenzyl α-isopropyl-4-chlorophenylacetate. The product, a colourless oil, was characterised by pmr spectroscopy. Chemical shift ppm (solvent CDCl₃): 0.69(3H, d, J=6 Hz, CH₃); 1.05 (3H, d of d, J=6 Hz and J=2 Hz, CH₃); 2.34(1H, m, CH(CH₃)₂); 3.27 (1H, d, J=10 Hz, CH); 7.17(1H, d of d, J=56 Hz and J=2 Hz, CHF) and c. 7.20(14H, m, aromatic protons).

EXAMPLE 7 α-CYANO-3-PHENOXYBENZYL α-FLUORO-α-ISOPROPYL-4-CHLOROPHENYLACETATE (22)

A mixture of α-fluoro-α-isopropyl-4-chlorophenylacetic acid (0.63 g), thionyl chloride (0.4 ml) and chloroform (2 ml) were heated under reflux for a period of 2 hours. The solvent and excess thionyl chloride were removed by distillation under reduced pressure and the product was added over a period of 15 minutes to a stirred solution of pyridine (0.3 ml), 3-phenoxybenzaldehyde cyanohydrin (0.8 ml of a 70% solution in diethyl ether) and diethyl ether (2 ml). The mixture was heated under reflux for a period of 2 hours and the solvent was removed by distillation under reduced pressure. The product was chromatographed over silica gel to give a colourless oil which was characterised by pmr spectroscopy. Chemical shift δppm (solvent CDCl₃); 0.75(3H, d, J=7 Hz, CH₃); 1.04 (3H, d, J=7 Hz, CH₃); 2.63(1H, m, —CH(CH₃)₂); 6.38 and 6.40(1H, 2xs, CH-CN) and c. 7.25(13H, m, aromatic protons).

EXAMPLE 8 α-FLUORO-3-PHENOXYBENZYL α-ISOPROPYL-(3,4-DICHLOROPHENYL)ACETATE (23)

This compound was prepared from α-isopropyl-(3,4-dichlorophenyl)acetic acid and α-fluoro-3-phenoxybenzylbromide following the procedure described in Example 2 Method B. The product, a colourless oil, was characterised by pmr spectroscopy. Chemical shift δppm (solvent CDCl₃): 0.76 (3H, d, J=6 Hz, CH₃); 1.07 (3H, d of d, J=6 Hz and J=2 Hz, CH₃); 2.33 (1H, m, —CH(CH₃)₂); 3.28 (1H, d, J=10 Hz, CH); 7.24 (1H, d of d, J=56 Hz and J=2 Hz, CHF) and about 7.33 (12H, m, aromatic protons).

EXAMPLE 9

α-Fluoro-3-phenoxybenzyl 3-(2-chloro-2-trifluoromethylvinyl)2,2-dimethylcyclopropanecarboxylate (4)

This compound was prepared from 3-(2-chloro-2-trifluoromethylvinyl)-2,2-dimethylcyclopropanecarboxylic acid and α-fluoro-3-phenoxybenzyl bromide following the procedure described in Example 2 Method B. The product, a colourless oil, was characterised by pmr spectroscopy. Chemical shift δppm (solvent CDCl₃): 1.26 (6H, m, C(CH₃)₂); 1.72–2.44 (2H, m, cyclopropyl protons); 5.80 and 6.18 (1H, 2xd, vinyl proton); 7.20 (1H, d, J=56 Hz, CHF) and about 7.13 (9H, m, aromatic protons).

EXAMPLE 10

3-(2,2-Dichlorovinyloxy)-α-fluorobenzyl α-isopropyl-(4-chlorophenyl)acetate (8)

This compound was prepared from α-isopropyl-4-chlorophenyl)acetic acid and 3-(2,2-dichlorovinyloxy)α-fluorobenzylbromide following the procedure described in Example 2 Method B. The product, a colourless oil, was characterised by pmr spectroscopy. Chemical shift δppm (solvent CDCl₃): 0.78 (3H, d, J=6 Hz, CH₃); 1.12 (3H, d of d, J=6 Hz and J=2 Hz, CH₃); 2.24 (1H, m, —CH(CH₃)₂); 3.33 (1H, d, J=10 Hz, CH); 7.27 (1H, d, J=56 Hz, CHF); about 7.25 (9H, m, vinyl and aromatic protons).

EXAMPLE 11

α-Fluoro-3-phenoxybenzyl 3-(2-methylprop-1-enyl)-2,2-dimethylcyclopropanecarboxylate (5)

This compound was prepared from 3-(2-methylprop-1-enyl)-2,2-dimethylcyclopropanecarboxylic acid and α-fluoro-3-phenoxybenzylbromide following the procedure described in Example 2 Method B. The product, a colourless oil, was characterised by pmr spectroscopy. Chemical shift δppm (solvent CDCl₃): 1.24 (6H, m, C(CH₃)₂); 1.70 (6H, s, (CH₃)₂C=); about 1.9 (2H, m, cyclopropyl protons); 4.93 and 5.43 (1H, 2xd, J=7 Hz, vinyl proton); 7.13 (1H, d, J=56 Hz, CHF); about 7.1 (9H, m, aromatic protons).

EXAMPLE 12

α-Fluoro-3-phenoxybenzyl α-isopropyl-(4-methoxyphenyl)acetate (2)

This compound was prepared from α-isopropyl-(4-methoxyphenyl)acetic acid and α-fluoro-3-phenoxybenzylbromide following the procedure described in Example 2 Method B. The product, a colourless oil, was characterised by pmr spectroscopy. Chemical shift δppm (solvent CDCl₃): 0.72 (3H, d, J=6 Hz, CH₃); 1.06 (3H, d of d, J=6 Hz and J=2 Hz, CH₃); about 2.25 (1H, m, —CH(CH₃)₂); 3.17 (1H, d, J=10 Hz, CH); 3.76 (3H, s, CH₃O); 7.18 (1H, d of d, J=56 Hz and J=2 Hz, CHF); about 7.2 (13H, m, aromatic protons).

EXAMPLE 13

α,2,3,4,5,6-Hexafluorobenzyl 3-(2,2-dichlorovinyl)-2,2-dimethylcyclopropanecarboxylate (24)

(a) Pentafluorobenzyl Fluoride

A mixture of pentafluorobenzyl alcohol (3.0 g) and dry methylene dichloride (50 ml) was cooled to a temperature of 0° C. in an ice-bath and 2-chloro-1-diethylamino-1,1,2-trifluoroethane (4.3 g) was slowly added to the cooled, stirred mixture over a period of ten minutes. After standing for a period of 18 hr at 0° C. the reaction mixture was poured into ice and the organic layer was separated and washed with IM aqueous sodium carbonate solution. The organic layer was dried over anhydrous sodium sulfate, the solvent was removed by distillation and the product was distilled under reduced pressure to give pentafluorobenzyl fluoride, b.p. 51° C. at 30 mm Hg.

(b) α-Bromopentafluorobenzyl Fluoride.

A mixture of pentafluorobenzyl fluoride (0.37 g), N-bromosuccinimide (0.36 g) and dry carbon tetrachloride (30 ml) was heated under reflux and irradiated with ultra violet light for a period of 4 hr. The reaction mixture was cooled, the insoluble material was removed by filtration and the solvent was removed by distillation under reduced pressure to give α-bromopentafluorobenzyl fluoride. The product was characterised by p.m.r. spectroscopy. Chemical shift δppm (solvent CDCl$_3$): 7.63 (d, J=48 Hz).

(c) α,2,3,4,5,6-Hexafluorobenzyl 3-(2,2-dichlorovinyl)2,2-dimethylcyclopropanecarboxylate was prepared from 3-(2,2-dichlorovinyl)-2,2-dimethyl-cyclopropanecarboxylic acid and α-bromopentafluorobenzyl fluoride following the procedure described in Example 2 Method B. The product, a colourless oil, was characterised by p.m.r. spectroscopy. Chemical shift δppm (solvent CDCl$_3$): 1.0–2.5 (8H, m, (CH$_3$)$_2$ and cyclopropyl protons); 5.67 and 6.24 (1H, both d of d, J=8 Hz and J=2 Hz, CH=); 7.53 (1H, d, J=52 Hz, CHF).

EXAMPLE 14

The Example demonstrates the insecticidal properties of compounds of the invention.

The activity of the compounds of the invention was tested against a variety of insect and other invertebrate pests. The test preparations were made by dissolving the compounds in a mixture of solvents consisting of 4 parts by volume of acetone and 1 part by volume of diacetone alcohol. The solutions were then diluted with water containing 0.01% by weight of a wetting agent sold under the name of "Lissapol" NX until the liquid preparations contained the required concentration of the compound ("Lissapol" is a Trade Mark).

The test procedure adopted for each pest was essentially the same and comprised supporting a number of the pests on a medium which was usually a host plant or a foodstuff on which the pests feed, and treating either or both the pests and the medium with the preparations.

The mortality of the pests was then assessed at periods usually varying from one to three days after the treatment.

The results of the tests are given below in Table 6. In this table the symbols used have the following meanings: "COMPOUND NO" indicates the test compound as defined by reference to Table 5. "RATE" indicates the concentration of active ingredient used expressed in parts per million.

The pest species used in the test are identified by the following code:

| "AF" | Aphis fabae |
| "AC" | Aphis craccivora |
| "MV" | Megoura viceae |
| "PM" | Plutella maculipennis |
| "PC" | Phaedon cocheariae |
| "MD" | Musca domestica |

An asterisk (*) in the table indicates that the test compound and anti-feedant activity i.e. the pest would not eat the treated host plant or foodstuff. A dash (-) in the table indicates that no test was carried out.

TABLE 6

| Compound No | Rate ppm | PERCENTAGE KILL OF TEST SPECIES | | | | | |
|---|---|---|---|---|---|---|---|
| | | AF | AC | MV | PM | PC | MD |
| 1 | 100 | 30 | 70 | 100 | 100* | 70* | 70 |
| 1 | 25 | 10 | — | 100 | 70* | 70* | 40 |
| 1 | 12.5 | 10 | — | — | 40* | 40* | 30 |
| 3 | 100 | 100 | 100 | 0 | 100* | 60* | 90 |
| 3 | 25 | 100 | — | 0 | 60* | 10* | 80 |
| 3 | 12.5 | 80 | — | 10 | 0* | 0* | 80 |
| 21 | 100 | 30 | — | 0 | 30* | 20* | 0 |
| 21 | 25 | 0 | — | 0 | 25* | 10* | 0 |
| 22 | 100 | 0 | — | 0 | 20* | 0* | 40 |
| 22 | 25 | 0 | — | 0 | 10* | 0* | 30 |
| 4 | 12.5 | 90–100 | — | 90–100 | 90–100* | 20 | 90–100 |
| 4 | 6.3 | 90–100 | — | 90–100 | 90–100* | 20 | 90–100 |
| 4 | 3.1 | 90–100 | — | 90–100 | 90–100* | 20 | 0 |

EXAMPLE 15

This Example demonstrates the ixodicidal activity of compounds of the invention against cattle tick (Boophilus microplus).

A suspension of each of the products was prepared by ball milling 10 parts of the product with 985 parts of water and 5 parts of "Teric" N9 ("Teric" is a Registered Trade Mark and "Teric" N9 is a nonionic surfactant obtained by condensing nonylphenol with ethylene oxide in a molar ratio of 1:9) to give a composition containing 1.0% active ingredient. A portion of each of the above suspension was then diluted with water to give compositions containing 0.1% and 0.01% active ingredient.

The efficacy of each of the products against engorged adult female ticks of the "Yeerongpilly" strain was tested by applying a microdrop of the appropriate concentration suspension to each of about twenty of the ticks. After 14 days the mortality count of the adult ticks was assessed by counting the eggs laid by them and the percentage of those eggs which had hatched. The results are given in Table 7.

The efficacy of each of the products against larval ticks of the "Yeerongpilly" strain was tested as follows: A sheet of filter paper was soaked in the appropriate concentration suspension and then allowed to dry. The treated paper was converted to the form of an envelope and approximately 100 larval ticks of the "Yeerongpilly" strain were enclosed therein. A mortality count was done on the larval ticks 48 hours after they had been placed in the envelope and the kill rated on a 0–5 scale wherein

| 0 represents | 0–20% kill |
| 1 represents | 20–50% kill |
| 2 represents | 50–80% kill |
| 3 represents | 80–95% kill |
| 4 represents | 95–99% kill |
| 5 represents | 100% kill |

The results are given in Table 7.

TABLE 7

| Compound No | % MORTALITY OF ADULTS | | KILL RATING AGAINST LARVAE | | |
|---|---|---|---|---|---|
| | 1% a.i. | 0.1% a.i. | 1% a.i. | 0.1% a.i. | 0.01% a.i. |
| 1 | 30 | 10 | 5 | 5 | 4 |
| 2 | 20 | 10 | 5 | 5 | 4 |
| 3 | 100 | 70 | 5 | 5 | 3 |
| 4 | 100 | 70 | 5 | 5 | 4 |

TABLE 7-continued

| Com-pound No | % MORTALITY OF ADULTS | | KILL RATING AGAINST LARVAE | | |
|---|---|---|---|---|---|
| | 1% a.i. | 0.1% a.i. | 1% a.i. | 0.1% a.i. | 0.01% a.i. |
| 23 | 90 | 10 | 5 | 5 | 3 |

EXAMPLE 16

This Example demonstrates the ixodicidal activity of compounds of the invention against cattle tick (*Boophilus microplus*).

An emulsion of each test compounds was prepared by mixing 25 parts of the compound with 75 parts of cyclohexanone and 25 parts of "Teric" N9 and diluting the mixture with water to provide the required concentration of active ingredient. Each of the emulsions so obtained was sprayed, to drippoint, onto calves heavily infested with various stages of the resistant "Biarra" strain of cattle tick. The efficacy of each of the compounds was assessed as follows:

(i) All adult female ticks which were fully engorged at the time of spraying were collected soon after spraying the calves. They were then placed in a Petri dish in an incubator for assessment of mortality based on capacity to lay eggs, and if eggs were laid, the viability of the eggs as shown by hatch of viable larvae. Engorged adults, if any, were also collected at 24 hours and 48 hours after spraying and the same assessment of mortality was made. This assessment is referred to as "Mortality-Engorged Adults" and the results, given in Table 8, are expressed as % mortality.

(ii) At daily intervals predetermined sampling areas on each calf were inspected for the effect of the active ingredient on the immature adults and nymphs. This assessment was rated on the 0-5 scale defined in Example 15 and is referred to as "Mortality-Immature Adults" and "Mortality-Nymphs". The results are given in Table 8.

TABLE 8

| Compound No | % Active Ingredient | Mortality | | |
|---|---|---|---|---|
| | | Engorged Adults (%; <24 hr/24 hr/48 hr) | Immature Adults* | Nymphs* |
| 2 | 0.1 | —/—/100 | 4 | 4-5 |
| 4 | 0.025 | 25/—/— | 4 | 5 |
| 23 | 0.1 | —/—/— | 4 | 4 |

EXAMPLE 17

This Example demonstrates the insecticidal activity of the compounds of the invention against adult *Musca domestica*.

In each test 20 flies (3-7 days old) were placed in a jar of 350 ml volume and the jar was sprayed with 0.2 ml of an acetone solution containing the test compound. Mortality was assessed after the jar had been allowed to stand for 24 hours at a temperature of 27° C.

Each compound was tested over a range of concentrations and the concentraton required to kill 50% of the flies ($LC_{50}$ in parts per million) was determined by plotting the mortality versus the log of the reciprocal of the insecticide population. The results are given in Table 9.

TABLE 9

| Compound No | $LC_{50}$ (ppm) |
|---|---|
| 1 | 80 |
| 3 | 60 |
| 4 | 36 |
| 23 | 160 |

We claim:
1. An ester of the formula

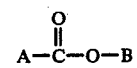

wherein:
A is the group

wherein:
V is the group

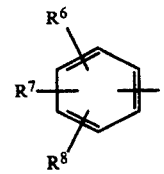

in which $R^6$, $R^7$ and $R^8$ are independently chosen from the group consisting of hydrogen, halogen, cyano, nitro, $C_1$ to $C_6$ alkyl optionally substituted with halogen atoms or $C_1$ to $C_6$ alkoxy, $C_2$ to $C_6$ alkenyl optionally substituted with halogen atoms, $C_2$ to $C_6$ alkynyl optionally substituted with halogen atoms, $C_1$ to $C_6$ alkoxy and $C_1$ to $C_6$ alkylthio;
W is chosen from the group consisting of $C_1$ to $C_6$ alkyl optionally substituted with halogen, $C_2$ to $C_6$ alkenyl optionally substituted with halogen and $C_2$ to $C_6$ alkynyl;
X is chosen from hydrogen and fluorine; and
B is the group

wherein:
Q is chosen from

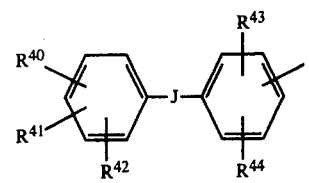

in which in which $R^{40}$, $R^{41}$, $R^{42}$, $R^{43}$ and $R^{44}$ are independently chosen from hydrogen, $C_1$ to $C_6$ alkyl, halogen and $C_2$ to $C_6$ alkenyl and J is oxygen; T is chosen from hydrogen, halogen, cyano, $C_1$ to $C_6$ alkyl optionally substituted with halogen, $C_2$ to $C_6$ alkenyl and $C_2$ to $C_6$ alkynyl; and X in the B substituent is as defined above for A with the proviso that at least one of the X substitutents is fluorine.

2. An ester according to claim 1 wherein $R^6$, $R^7$ and $R^8$ are independently chosen from hydrogen, halogen and $C_1$ to $C_6$ alkoxy;

W is chosen from $C_1$ to $C_6$ alkyl; and

X is chosen from hydrogen and fluorine; and

Q is chosen from the group in which $R^{40}$, $R^{41}$, $R^{42}$ are hydrogen, $R^{43}$ and $R^{44}$ are chosen from hydrogen and halogen and J is oxygen;

and T is chosen from hydrogen and cyano.

3. An ester according to claim 1 or claim 2 wherein in the group A,

V is chosen from the groups phenyl, 4-chlorophenyl, and 4-methoxyphenyl;

W is isopropyl; and

X is hydrogen; and wherein in the group B,

Q is chosen from groups 3-phenoxyphenyl and 3-(2,2-dichlorovinyloxy)phenyl;

T is hydrogen; and

X is fluorine.

4. The compound α-fluoro-3-phenoxybenzyl-α-isopropyl-4-chlorophenylacetate.

5. An insecticidal or acaricidal composition comprising as active ingredient an insecticidally or acaricidally effective amount of a compound according to claim 1 and an inert carrier therefor.

6. A composition according to claim 5 additionally comprising a surface-active agent.

7. A composition according to claim 5 additionally comprising an insecticide synergist.

8. A process for combatting or controlling infestations of insect or acarine pests which process comprises applying to said pests, to the locus of said pests or to the habitat of said pests an insecticidally or acaricidally effective amount of a compound according to claim 1.

9. A process according to claim 8 wherein the compound or composition is applied to a growing plant.

10. A process according to claim 8 wherein the compound or composition is applied to a domestic animal.

11. A process according to claim 8 wherein the compound or composition is applied to cattle infested with ixodid ticks.

* * * * *